United States Patent
Lavi

(10) Patent No.: US 8,628,582 B2
(45) Date of Patent: Jan. 14, 2014

(54) SUBTALAR IMPLANT AND METHODS OF USE THEREOF

(75) Inventor: Abraham Lavi, Pittsburgh, PA (US)

(73) Assignee: Vilex in Tennessee, Inc., McMinnville, TN (US)

( * ) Notice: Subject to any disclaimer, the term of this patent is extended or adjusted under 35 U.S.C. 154(b) by 638 days.

(21) Appl. No.: 11/508,121

(22) Filed: Aug. 22, 2006

(65) Prior Publication Data

US 2007/0173954 A1 Jul. 26, 2007

Related U.S. Application Data

(60) Provisional application No. 60/710,336, filed on Aug. 22, 2005.

(51) Int. Cl.
*A61F 2/42* (2006.01)
*A61F 2/00* (2006.01)
*A61F 2/08* (2006.01)
*A61B 17/58* (2006.01)
*A61B 17/60* (2006.01)
*A61B 17/04* (2006.01)

(52) U.S. Cl.
USPC ............................ 623/21.18; 606/99; 606/300

(58) Field of Classification Search
USPC .................. 606/300, 301, 304, 323, 329, 99; 623/17.11, 21.18; 411/17, 395
See application file for complete search history.

(56) References Cited

U.S. PATENT DOCUMENTS

| | | | |
|---|---|---|---|
| 5,116,337 A | 5/1992 | Johnson | |
| 5,782,919 A * | 7/1998 | Zdeblick et al. | 623/17.16 |
| 6,136,032 A * | 10/2000 | Viladot Perice et al. | 623/21.18 |
| 6,168,631 B1 | 1/2001 | Maxwell et al. | |
| 7,008,453 B1 * | 3/2006 | Michelson | 623/17.16 |
| 8,092,547 B2 * | 1/2012 | Lepow et al. | 623/21.18 |
| 2002/0068938 A1 * | 6/2002 | Jackson | 606/61 |
| 2004/0167526 A1 * | 8/2004 | Jackson | 606/73 |
| 2005/0177165 A1 * | 8/2005 | Zang et al. | 606/73 |
| 2005/0177243 A1 * | 8/2005 | Lepow et al. | 623/21.11 |
| 2005/0187636 A1 * | 8/2005 | Graham | 623/21.18 |
| 2008/0215155 A1 * | 9/2008 | de Villiers et al. | 623/17.16 |
| 2009/0099664 A1 * | 4/2009 | Forrester | 623/21.18 |

OTHER PUBLICATIONS

Lepow et al., "A New Generation of Subtalar Implants", Podiatry Management, Oct. 2004, pp. 143-148.
Dockery et al., "The Maxwell-Brancheau Arthroereisis (MBA) Implant in Pediatric and Adult Flexible Flatfoot Conditions", Foot and Ankle Quarterly, Winter 1999, vol. 12, No. 4, pp. 107-120.

* cited by examiner

*Primary Examiner* — David Bates
(74) *Attorney, Agent, or Firm* — Barbara E. Johnson, Esq.

(57) ABSTRACT

The present invention provides a subtalar implant as well as methods of use thereof for the purpose of correcting podiatric disorders such as various types of flat foot conditions relating to the subtalar joint. The subtalar implant is capable of threaded engagement with a positioning element used to position and manipulate the implant during surgical implantation in the sinus tarsi of the foot. The implant is cannulated to receive a guide rod to facilitate final positioning of the implant. Once implanted, the subtalar implant provides anatomical fit with the subtalar joint anatomical structure without the need for indentations to receive osseous tissue growth to anchor the subtalar implant.

17 Claims, 4 Drawing Sheets

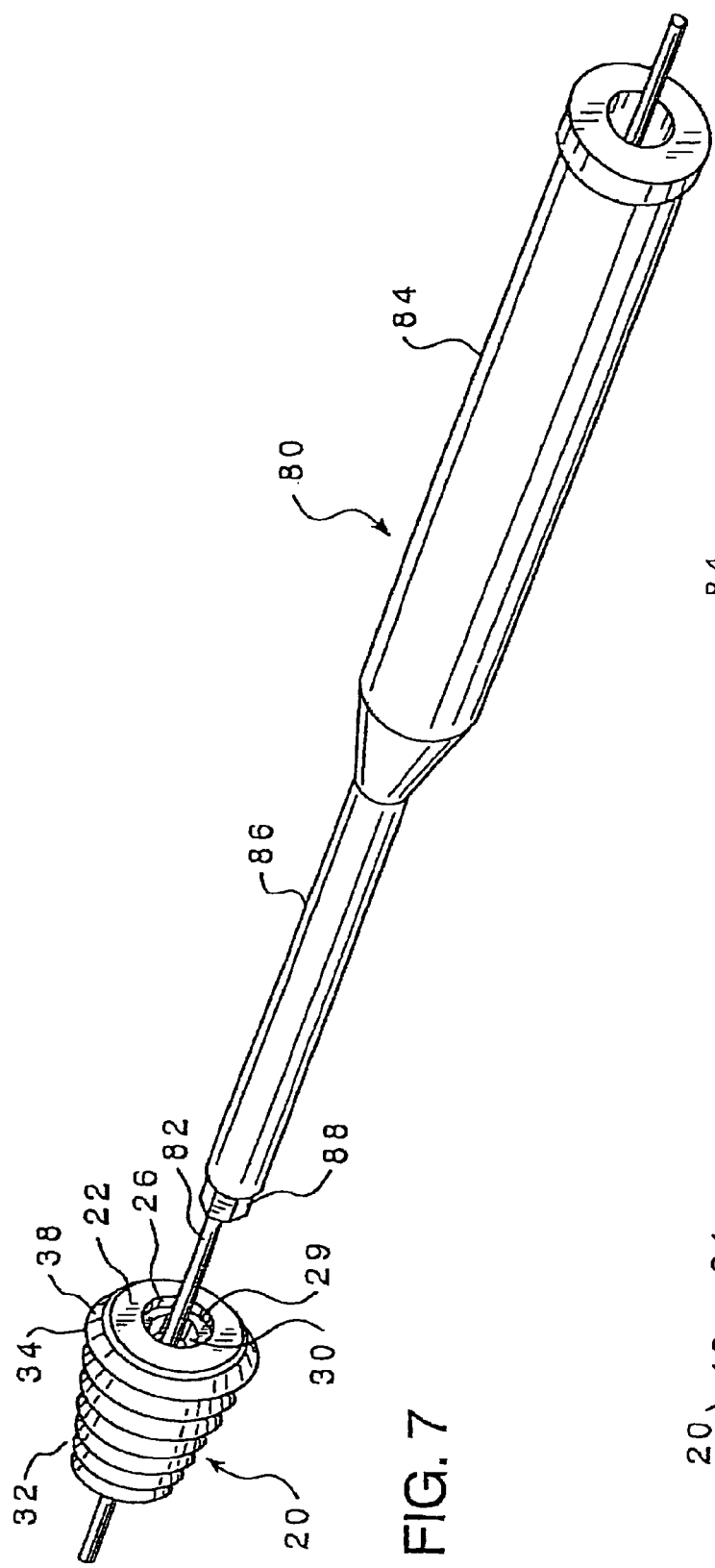
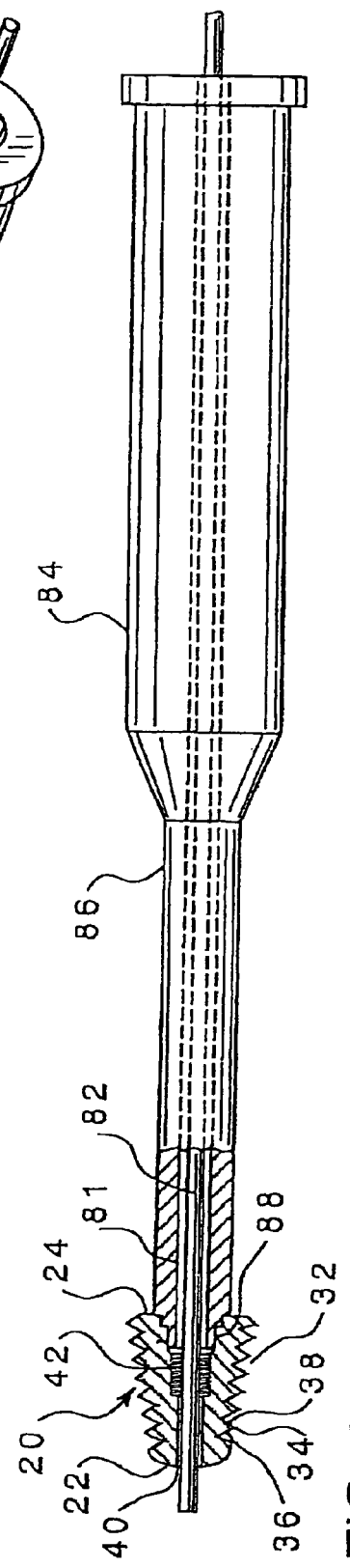
FIG. 7
FIG. 8

SUBTALAR IMPLANT AND METHODS OF USE THEREOF

CROSS REFERENCE TO RELATED APPLICATION

The present application claims priority to U.S. Provisional Application No. 60/710,336, filed Aug. 22, 2005, which is incorporated herein by reference.

BACKGROUND OF THE INVENTION

1. Field of the Invention

The present invention relates to a surgical implant in the nature of a subtalar implant and the method of use thereof for implantation to correct podiatric disorders.

2. Description of Related Art

A subtalar joint (STJ) arthroereisis is provided as well as methods of use thereof for the purpose of correcting podiatric disorders such as various types of flat foot conditions relating to the STJ. The STJ arthroereisis is surgically implanted in the sinus tarsi. The sinus tarsi is a conical-shaped cavity located between the anterosuperior surface of the calcaneus and the inferior aspect of the neck of the talus. Opening laterally, the sinus tarsi is anterior to the fibular malleolus and terminates posteromedially directly behind the sustentaculum tali. Once implanted, the STJ arthroereisis functions primarily to preserve the STJ while also to limit excessive valgus motion and calcaneal eversion and to limit anterior and plantar migration of the talus.

The development of STJ arthroereisis for correcting podiatric disorders including flat foot conditions dates back to 1946. The original STJ arthroereisis incorporated a theory of using a bone graft to elevate the sinus tarsi and to limit pronation of the subtalar joint. Procedures built upon the bone grafting techniques to eliminate pronation by positioning a bone graft or a custom carved silicone wedge inside the sinus tarsi. The bone grafts and silicone wedges were further developed into a stemmed polyethylene block known better as the STA-peg, which was further modified through time. The bone grafts, the silicone wedges, and the stemmed polyethylene block were later replaced with modern, threaded implants for surgical implantation within the sinus tarsi. For example, the Maxwell-Brancheau Arthroereisis (MBA) implant is a cannulated, soft-threaded screw-shaped cylindrical prothesis manufactured from a premium titanium alloy. Newer generation threaded implants developed as a conical subtalar implant (CSI), which is a cannulated, soft-threaded conical prothesis, and a domed-stemmed subtalar implant (DSI), which is a cannulated, domed and stemmed prothesis, both of which are manufactured from a premium titanium alloy.

While initially described as a simple bone graft to elevate the floor of the sinus tarsi, STJ arthroereisis has developed into a modern generation of implants. The outcomes anticipated from STJ arthroereisis with the modern implants include a decrease in frontal plane heel valgus, an improved medial arch height while bearing weight, a decreased pronatory motion of the STJ, a decreased mid-tarsal joint (MTJ) inversion and eversion, and a spared STJ inversion. Additionally, STJ arthroereisis with the modern implants provide a re-alignment of previously anteriorly displaced cyma line, decreased talo-navicular joint (TNJ) subluxation and talar declination, and an increased calcaneal inclination.

Several problems are associated with the modern implants for STJ arthroereisis. The features of modern implants lack positioning control capabilities for use during implantation surgery, which requires precise and controlled manipulation of the implant for final positioning. Additionally, the geometric shape of the modern implants is either cylindrical or conical. Modem cylindrically-shaped implants provide poor anatomical fit with the STJ structure. Modem conically-shaped implants may offer a slightly better fit with STJ anatomical structure than cylindrically-shaped implants, but require apertures along the softened thread surface for post implantation osseous tissue growth to stabilize the implant.

Accordingly, the subtalar implant of the present invention overcomes the problems associated with modern implants for STJ arthroereisis. In accordance with the present invention, the subtalar implant is capable of threaded engagement with a positioning element, which is used for positioning control and manipulation of the subtalar implant during surgical implantation. For assistance in final positioning for implantation, the subtalar implant is cannulated to receive a guide rod to facilitate proper positioning of the subtalar implant with a cannulated driver. Once implanted, the subtalar implant of the present invention provides a superior anatomical fit with the STJ anatomical structure, without the need for osseous growth indentations to anchor the subtalar implant.

SUMMARY OF THE INVENTION

The present invention provides a subtalar implant capable of threaded engagement with a positioning element, which is used for positioning control and manipulation of the subtalar implant during surgical implantation. For assistance in final positioning for implantation, the subtalar implant is cannulated to receive a guide rod to facilitate proper positioning of the subtalar implant with a cannulated driver. Once implanted, the subtalar implant of the present invention provides anatomical fit with the STJ anatomical structure without the need for indentations to receive osseous tissue growth to anchor the subtalar implant.

The conically-shaped subtalar implant comprises a low domed distal end, a threaded surface of a concentric v-shaped thread, and a flat proximal end. A cannulation is provided centrally along the longitudinal axis of the subtalar implant. Female threads are provided in a section of the cannulation. At the proximal end of the female threads of the subtalar implant, the cannulation expands through a neck into a fitting recess. The fitting recess expands through a shoulder into a cylindrical recess.

The positioning element comprises a cylindrical rod with a male thread at its distal end. The male thread is adapted to engage the female threads in the cannulation of the subtalar implant.

During surgical implantation, the male threads of the positioning element engage the female threads of the cannulation of the subtalar implant, and the positioning element is used for positioning control and manipulation of the subtalar implant into the sinus tarsi of a foot during surgery. Once the subtalar implant is properly positioned in the sinus tarsi, the positioning element is twisted to unscrew the male threads from the female threads in the cannulation of the subtalar implant, and the positioning element is removed from the subtalar implant positioned in the sinus tarsi. A head of a driver is positioned in the fitting recess of the subtalar implant, and a guide rod is positioned in a cannulation of the driver and corresponding cannulation of the subtalar implant. The guide rod is used as a point of reference to ensure proper positioning of the subtalar implant as it is being screwed into final position in the sinus tarsi by the driver.

BRIEF DESCRIPTION OF THE DRAWINGS

FIG. 7 illustrates an exploded view of the subtalar implant, a guide rod and a driver in accordance with the present invention; and FIG. 8 illustrates a partial sectional side view of the subtalar implant engaged with the head of the driver all in line with a guide rod.

DESCRIPTION OF THE PREFERRED EMBODIMENTS

Figures 1, 2:
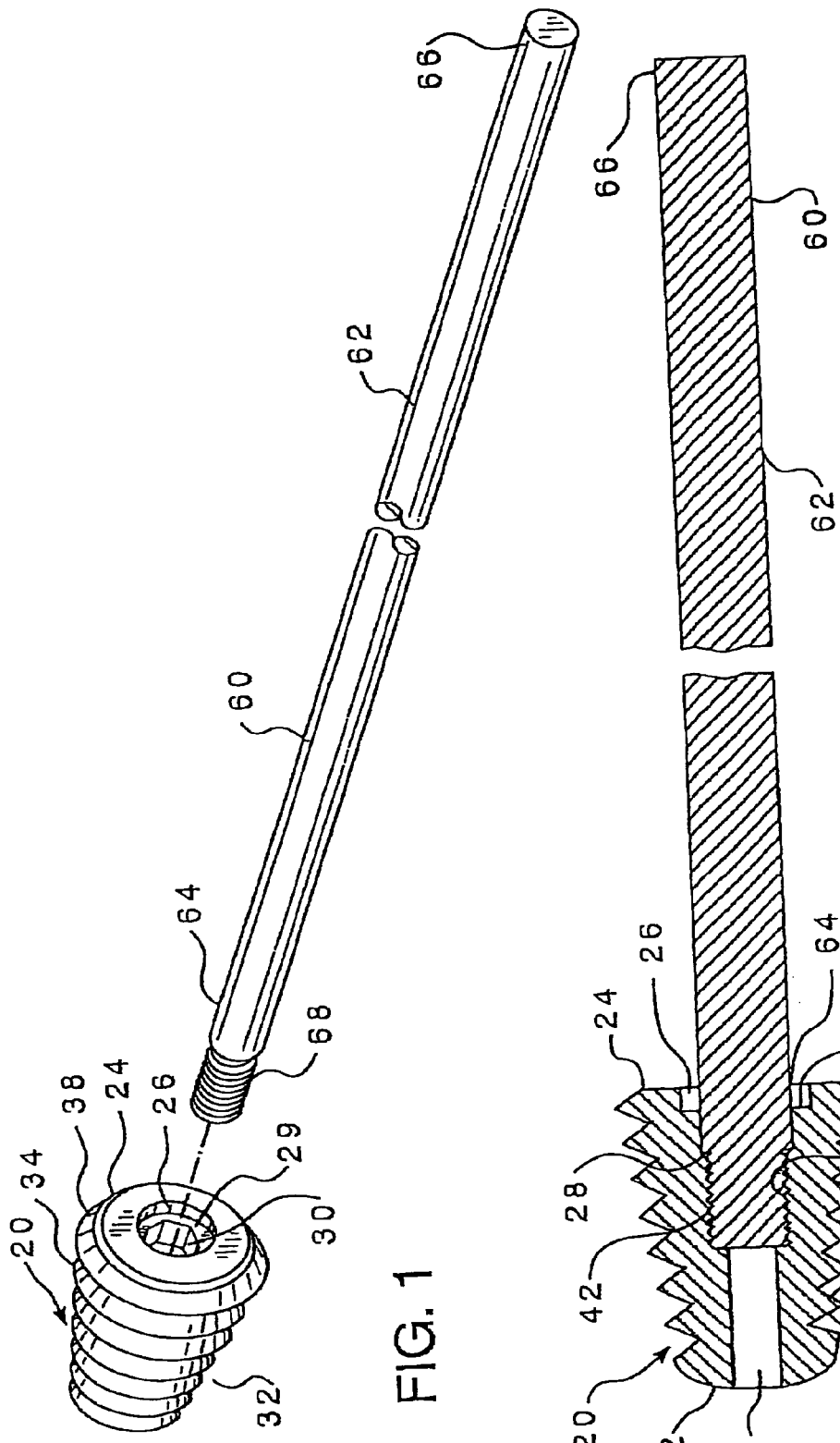
FIG. 1 illustrates an exploded view of the subtalar implant and positioning element in accordance with the present invention.
FIG. 2 illustrates a sectional view of the side of the subtalar implant engaging the positioning element in accordance with the present invention.
Figure 3:
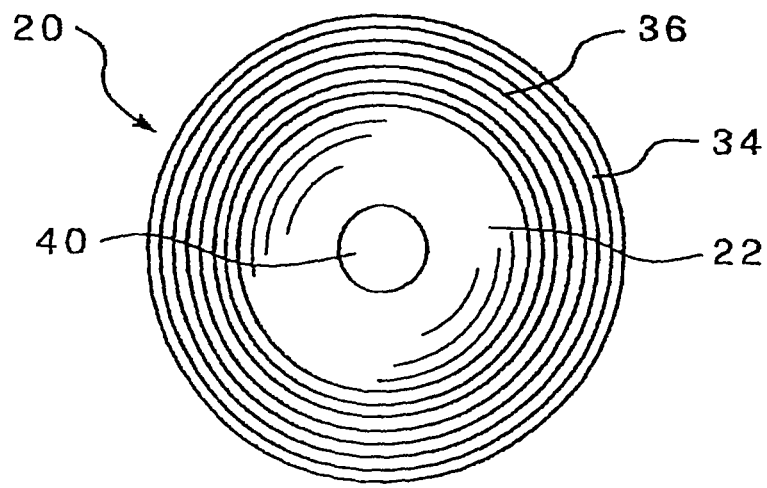
FIG. 3 illustrates a perspective view of the distal end of the subtalar implant.
Figure 4:
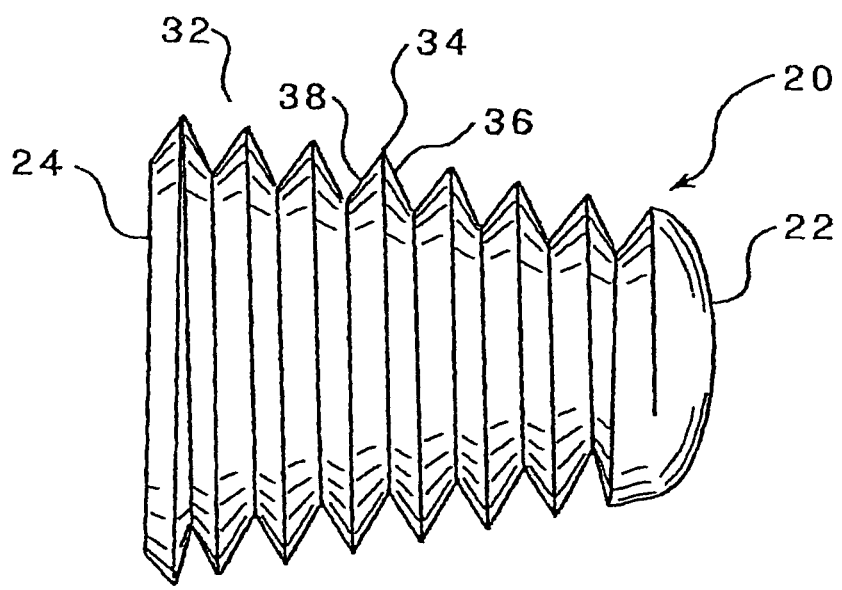
FIG. 4 illustrates a perspective view of the side of the subtalar implant.
Figure 5:
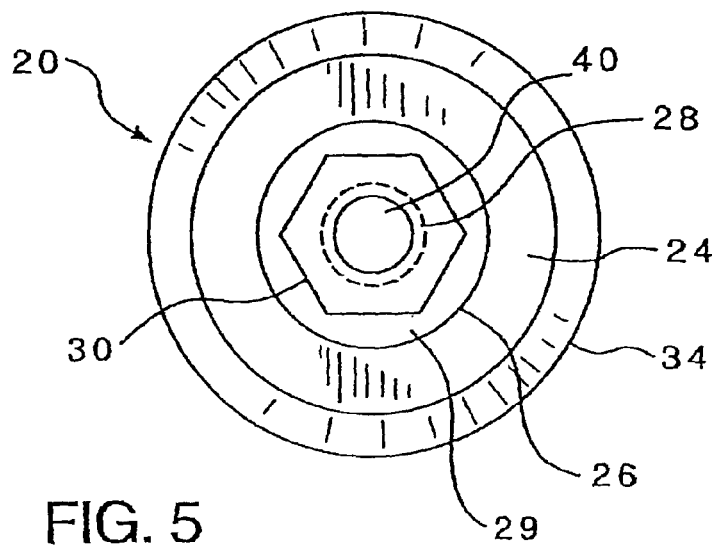
FIG. 5 illustrates a perspective view of the proximal end of the subtalar implant.

Referring to FIGS. 1 through 8 in which similar reference characters refer to similar parts throughout the several views thereof, the present invention comprises an implant 20 and a positioning element 60 and methods for using the positioning element 60 to position the implant 20 in the sinus tarsi adjacent the subtalar joint (STJ). The correct positioning of the implant 20 with the positioning element 60 in the sinus tarsi is essential for correcting manifestations of problems associated with various types of flat foot disorders.

Figure 6:
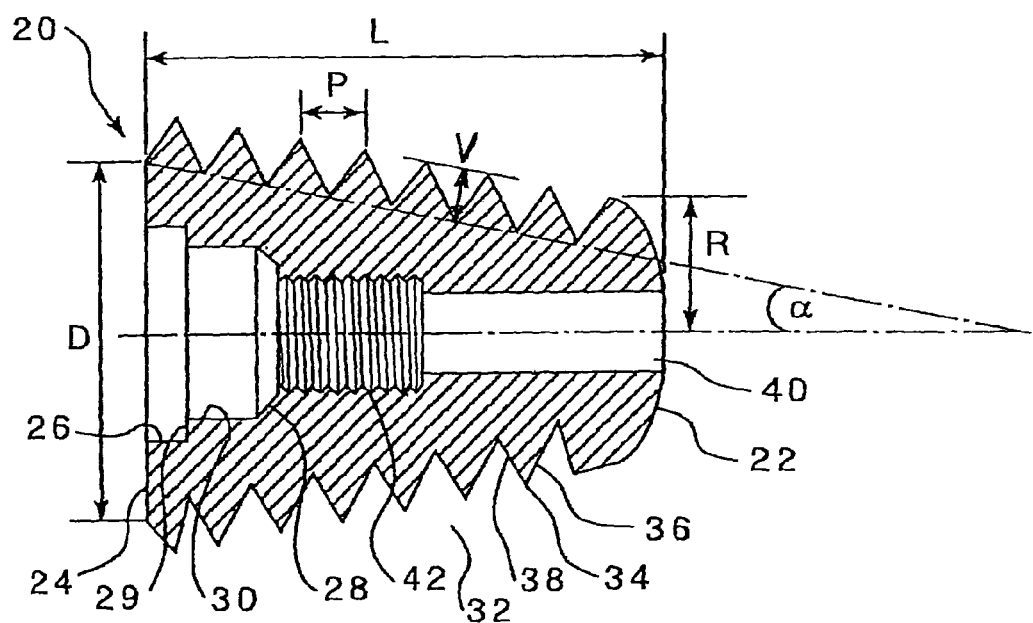
FIG. 6 illustrates a sectional view of the side of the subtalar implant.

Referring generally to FIGS. 1-8, the implant 20 is generally frustoconically shaped. The implant 20 is configured with the external features of a low domed distal end 22 with preferred radii, a threaded surface 32 with v-shaped threads 34, and a flat proximal end 24 with preferred diameters as shown particularly in FIGS. 4 and 6. The v-shaped threads 34 consist of one continuous thread that begins at the low domed distal end 22, wraps around the implant 20 to provide the threaded surface 32, and terminates adjacent the flat proximal end 24 of the implant 20. The v-shaped threads 34 have a leading edge 36 and a trailing edge 38 as shown in FIG. 6. Generally, the depth V of the v-shaped thread 34 has a 1.0 mm vertical distance between the trough and the peak of the v-shaped thread 34 as shown in FIG. 6. The implant 20 is configured with a less aggressive thread so as not to provide a leading edge with a greater height than a trailing edge, which are presented by threads of a self-tapping screw. All preferred sizes of the implant 20 have a thread pitch P of 2.15 mm. The thread pitch P is the measured distance between two sequential peaks of the v-shaped threads 34 as shown in FIG. 6.

Referring to FIG. 6, the frustoconical shape of the implant 20 is configured such that the angle α between the longitudinal midline and the threaded surface 32 provides a preferred shape for anatomical fit. The angle α provides the implant 20 with a preferred anatomical fit when the implant 20 is positioned in the sinus tarsi adjacent the STJ of a foot. The frustoconical shape of the implant 20 is provided by the preferred embodiments of the proximal end diameter D, angle α, length L, and distal end radius R as shown in FIG. 6.

The implant of the present invention can have several sizes, such as a proximal end diameter D of between about 4.0 mm to 20.0 mm, an angle α of between about 1.0 degree to 15.0 degrees, a length L of between about 10.0 mm to 20.0 mm, and a distal end radius R of between about 2.0 mm to 5.0 mm.

Several preferred sizes of the implant 20 are provided by the present invention. In one embodiment, the implant 20 has a proximal end diameter D of 8.0 mm, angle α of 10.0 degrees, length L of 14.6 mm, and a distal end radius R of 3.6 mm. In a second embodiment, the implant 20 has a proximal end diameter D of 9.0 mm, angle α of 8.1 degrees, length L of 14.7 mm, and a distal end radius R of 3.7 mm. In a third embodiment, the implant 20 has a proximal end diameter D of 10.0 mm, angle α of 6.1 degrees, length L of 14.8 mm, and a distal end radius R of 3.8 mm. In a fourth embodiment, the implant 20 has a proximal end diameter D of 11.0 mm, angle α of 4.3 degrees, length L of 14.9 mm, and a distal end radius R of 3.9 mm. In a fifth embodiment, the implant 20 has a proximal end diameter D of 12.0 mm, angle α of 2.1 degrees, length L of 15.0 mm, and a distal end radius R of 4.0 mm. The aforementioned preferred embodiments are provided for a preferred anatomical fit to correct flat foot conditions in various sized patients.

Referring generally to FIGS. 1-8, the implant 20 is configured with several internal features. One internal feature is a cylindrical recess 26 at the proximal end 24 of the implant 20. The cylindrical recess 26 is centered along the longitudinal axis of the implant 20. The cylindrical recess 26 has a diameter that is smaller than the diameter D of the proximal end 24 of the implant 20. The cylindrical recess 26 has a depth of approximately 2.0 mm into the proximal end 24 of the implant 20. The cylindrical recess 26 is continuous with a fitting recess 30. A shoulder 29 is provided with the implant 20, which delineates the end of the cylindrical recess 26 and the beginning of the fitting recess 30.

Referring generally to FIGS. 1-8, the fitting recess 30 of the implant 20 is configured to receive a corresponding fitting head 88 of a driver 80 used in the control and positioning of the implant 20 into and in the sinus tarsi of a foot. The fitting recess 30 is preferably hexagonal with a width of 4.0 mm from flat surface to flat surface of the recess. Other preferred embodiments of the fitting recess 30 are apparent to those skilled in the art and include a star shape, a D shape, a square shape and any other suitable shape. The fitting recess 30 of the implant 20 has a depth of 2.0 mm. The fitting recess 30 is in continuous communication with a female thread 42 of the implant 20.

Referring specifically to FIGS. 2 and 6, the female thread 42 of the implant 20 is positioned between the fitting recess 30 and a cannulation 40. The fitting recess 30 is connected through a neck 28 to the female thread 42 of the implant 20. The female thread 42 is configured in the circular wall adjacent the cannulation 40 of the implant 20 along a length of 4.0 mm. The female thread 42 can have either a left-hand or right-hand configuration. The female thread 42 is adapted for fit with a corresponding left hand or right-hand configured male thread 68 of the positioning element 60, which is rod shaped with a proximal end 66 and a distal end 64. The positioning element 60 may have a handle 62 or other gripping means to provide friction with the hand of an individual positioning the implant 20 during surgery so long as male threads 68 are provided at the distal end 64 of the positioning element 60. Other embodiments of the positioning element 60 would be apparent to a skilled artisan.

Referring specifically to FIGS. 2 and 6, a cannulation 40 is provided along the longitudinal axis of the implant 20. The cannulation 40 provides communication through the low domed distal end 22 along the longitudinal axis to the female thread 42 of the implant 20. Further communication is provided between the cannulation 40 through the proximal end 24 of the implant 20 by way of the female threads 42, fitting recess 30, and the cylindrical recess 26. Regardless of the size configuration of a preferred embodiment of the implant 20, the cannulation 40 has a uniform diameter of 2.0 mm in all embodiments. The cannulation 40 provides a receiving space for a guide rod 82 used during surgery.

The implant 20 and positioning element 60 are preferably made of a metal, for example, titanium or stainless steel.

During surgery, the implant 20 is positioned in the sinus tarsi adjacent the STJ as an STJ arthroereisis to correct flat foot conditions. The surgical procedure of STJ arthroereisis implantation is known by a skilled artisan. However, for the purposes of disclosing the method of the present invention, the relevant steps of STJ arthroereisis implantation are explained.

Prior to implantation of the implant 20, a single incision is made in the lateral side of the foot of a patient over the sinus tarsi. While incising, it is important to avoid cutting the intermediate dorsal cutaneous nerves and the sural nerve. The deep fascia of the foot should also be incised, and if encountered, the cervical ligament of the foot should be retracted for access to the sinus tarsi. The tarsal canal is dissected rendering palpable access to the calcaneous and talus. The sinus tarsi is minimally dissected.

Adjacent the lateral side of the foot, a probing instrument is positioned perpendicular to the lateral wall of the calcaneous and is inserted toward the medial aspect of the foot through the sinus tarsi into the sinus canalis. The tip of the instrument is pushed against the interior surface of the skin along the medial aspect of the foot. The tip of the instrument will present through tenting of the skin along the medial aspect of the foot. An incision is provided at the location of the tenting to provide through and through communication from the lateral side to the medial side of the foot.

A plastic implant is screwed into the sinus tarsi to open access to the sinus tarsi and open the sinus canalis. The plastic implant is also used partially as a positioning guide, and as an initial step, the implant is removed before final positioning of the implant 20. Once access to the sinus tarsi is opened, the male threads 68 of the positioning element 60 are screwed into the female threads 42 of the implant 20, and the implant 20 is positioned in the sinus tarsi for sizing. An appropriately sized implant 20 is selected for final positioning of the implant 20, which is controlled by the positioning element 60. Once the proper implant 20 is selected and positioned, the positioning element 60 is unscrewed from the implant 20. The guide rod 82 is then inserted through the cannulation 40 of the implant 20 so that the guide rod 82 fully communicates through the incision on the lateral aspect of the foot and through the incision on the medial aspect of the foot. The guide rod 82 is used to position the longitudinal axis of the implant 20 at a suitable angle from the longitudinal bisection of the talus. The distal end 22 of the implant 20 should not cross over the longitudinal bisection of the talus. The distance of the proximal end 24 of the implant 20 from the lateral surface of the calcaneous will vary depending upon the size of the implant 20 and the size of the patient.

In the proper position and at a suitable angle from the longitudinal bisection of the talus, the head 88 of the driver 80 (having handle 84 and shaft 86) is positioned in the fitting recess 30 of the implant 20 with the guide rod 82 still in position through cannulations 40, 81 of the implant 20 and the driver 80 as shown in FIGS. 7 and 8. With the head 88 of the driver 80 in the fitting recess 30, the driver 80 is used to turn the implant 20 either clockwise or counterclockwise into final position. The final position is the position at which the implant 20 acts to significantly reduce excess STJ pronation and other foot movement associated with the various types of flat foot conditions. Once the implant 20 is finally positioned, the driver 80 and the guide rod 82 are removed, and the deep tissue, fascia, subcutaneous and skin layers are closed in a manner that is acceptable in the art.

While the present invention is satisfied by embodiments in many different forms, there is shown in the drawings and described in detail herein the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

The invention claimed is:

1. A system for the surgical insertion of an implant into the sinus tarsi of a foot of a patient, comprising:
   a unitary frustoconical-shaped implant;
      wherein the frustoconical-shaped implant comprises a low domed distal end, an outer surface of v-shaped threads having a first handedness, and a flat proximal end, and the frustoconical-shaped implant is configured to be received within the sinus tarsi;
      wherein the vertical distance between a trough and a peak of each of said v-shaped threads is between about 0.5 mm to 1.5 mm;
      wherein the v-shaped threads do not have a leading edge with a greater height than a trailing edge and therefore are not threads of a self-tapping screw;
      wherein the frustoconical-shaped implant consists of one piece having a first cannulation entirely through a longitudinal axis thereof;
      wherein said first cannulation comprises a proximal polygonal fitting recess and a distal cylindrical recess;
      wherein said cylindrical recess is continuous with said fitting recess and said cylindrical recess contains internal threads;
      wherein the internal threads are left-handed or right-handed female threads positioned over no more than one-third of the length of said first cannulation;
      wherein said internal threads further have a second handedness opposite from the first handedness of said v-shaped threads;
      wherein said cannulation is concentric with said fitting recess and said cylindrical recess; and
      wherein a shoulder in said first cannulation of said implant delineates the end of said cylindrical recess and the beginning of said fitting recess;
   a positioning tool having a polygonal distal wrench head corresponding for engagement with the polygonal fitting recess in said frustoconical-shaped implant, and the positioning tool further having a second cannulation throughout an entire longitudinal axis of the positioning tool;
      wherein the positioning tool is capable of use in applying a rotating force and a pushing force to the frustoconical-shaped implant during insertion of said frustoconical-shaped implant into the sinus tarsi when the positioning tool is engaged with the polygonal fitting recess;
   a positioning element having threads which correspond for threading into and engaging said internal threads in said frustoconical-shaped implant;
      wherein the positioning element is capable applying a pulling force against the frustoconical-shaped implant during positioning or withdrawal of the implant relative to the sinus tarsi when threaded into and engaging the internal threads; and a guide rod dimensioned to fit within and pass through both said first cannulation and said second cannulation and capable of guiding the frustoconical-shaped implant and the positioning tool to the sinus tarsi.

2. The system of claim 1, wherein the vertical distance between a trough and a peak of each of said v-shaped threads is 1.0 mm.

3. The system of claim 1, wherein the distance between two sequential peaks of said v-shaped threads is between about 1.5 mm to 2.5 mm.

4. The system of claim 1, wherein the distance between two sequential peaks of said v-shaped threads is 2.15 mm.

5. The system of claim 1, wherein said frustoconical-shaped implant has a diameter of between about 4.0 mm to 20.0 mm at said proximal end, an angle α of between about 1.0 degree to 15 degrees, a length of between about 10.0 mm to 20.0 mm and a radius at said distal end of between about 2.0 mm to 5.0 mm.

6. The system of claim 1, wherein said frustoconical-shaped implant has a diameter of 8.0 mm at said proximal end, an angle α of 10.0 degrees, a length of 14.6 mm and a radius at said distal end of 3.6 mm.

7. The system of claim 1, wherein said frustoconical-shaped implant has a diameter of 9.0 mm at said proximal end, an angle α of 8.1 degrees, a length of 14.7 mm and a radius at said distal end of 3.7 mm.

8. The system of claim 1, wherein said frustoconical-shaped implant has a diameter of 10.0 mm at said proximal end, an angle α of 6.1 degrees, a length of 14.8 mm and a radius at said distal end of 3.8 mm.

9. The system of claim 1, wherein said frustoconical-shaped implant has a diameter of 11.0 mm at said proximal end, an angle α of 4.3 degrees, a length of 14.9 mm and a radius at said distal end of 3.9 mm.

10. The system of claim 1, wherein said frustoconical-shaped implant has a diameter of 12.0 mm at said proximal end, an angle α of 2.1 degrees, a length of 15.0 mm and a radius at said distal end of 4.0 mm.

11. The system of claim 1, wherein said cylindrical recess is centered along the longitudinal axis of said implant at said proximal end of said implant, and wherein said cylindrical recess has a diameter that is smaller than the diameter of said proximal end of said frustoconical-shaped implant.

12. The system of claim 1, wherein said cylindrical recess has a depth of about 2.0 mm into said proximal end of said frustoconical-shaped implant.

13. The system of claim 1, wherein said fitting recess has a polygonal shape selected from the group consisting of hexagonal, star shape, D shape, or square shape.

14. The system of claim 1, wherein said fitting recess is connected through a neck and is in continuous communication with said internal threads of said frustoconical-shaped implant.

15. The system of claim 1, wherein said fitting recess is hexagonal in shape having a depth of 2.0 mm and a width of 4.0 mm from flat surface to flat surface of said fitting recess.

16. The system of claim 1, wherein said internal threads are positioned between said fitting recess and said first cannulation of said frustoconical-shaped implant in the wall adjacent to said first cannulation, said female threads having a length of 4.0 mm.

17. The system of claim 1, wherein said first cannulation has a diameter of 2.0 mm.

* * * * *